United States Patent [19]

Brunner

[11] 4,052,441

[45] Oct. 4, 1977

[54] SEPARATION OF ACIDS AND ESTERS IN THE PROCESSING OF WASTE SALT SOLUTION OF CYCLOHEXANONE MANUFACTURE

[76] Inventor: Josef Klemens Brunner, Scheuchzerstrasse 47, Zurich, Switzerland

[21] Appl. No.: 620,306

[22] Filed: Oct. 7, 1975

[30] Foreign Application Priority Data

Oct. 10, 1974 Austria ................................. 8175/74

[51] Int. Cl.$^2$ .............................................. C07C 69/66
[52] U.S. Cl. ................................ 560/179; 260/533 R; 260/535 R; 260/537 R; 260/538; 560/204
[58] Field of Search ............ 260/484 R, 485 S, 535 R, 260/533 R, 537 R, 538

[56] References Cited

U.S. PATENT DOCUMENTS

| | | | |
|---|---|---|---|
| 2,824,123 | 2/1958 | Kuceski | 260/485 S |
| 2,904,584 | 9/1959 | Payne et al. | 260/484 R |
| 3,428,656 | 2/1969 | Weiss | 260/484 R |
| 3,590,080 | 6/1971 | Beesley et al. | 260/484 R |

*Primary Examiner*—Paul J. Killos
*Attorney, Agent, or Firm*—William R. Woodward

[57] ABSTRACT

After acidification and separation of a concentrated aqueous solution of sodium sulfate, the water-containing organic phase that remains is first distilled to remove mainly water, then chilled to crystallize out the bulk of the dicarboxy acids, then esterified and distilled again to obtain monocarboxy acid esters in distillate fractions, after which the residue is further esterified to facilitate obtaining the remaining dicarboxy acids in usable form.

8 Claims, No Drawings

SEPARATION OF ACIDS AND ESTERS IN THE PROCESSING OF WASTE SALT SOLUTION OF CYCLOHEXANONE MANUFACTURE

In the manufacture of cyclohexanone by catalytic oxidation of cyclohexane with oxygen, a reaction mixture is produced that contains, along with the desired products, larger quantities of various saturated monocarboxylic and dicarboxylic acids. Before further treatment of the reaction mixture, water and/or alkali solutions are added to the acids so that they are obtained in the form of a concentrated aqueous solution of their salts. Such solutions are an inconvenient byproduct of cyclohexanone production. They contain more or less the following carboxylic acid quantities in the form of their sodium salts:

| Acids | Percent by Weight |
| --- | --- |
| formic | 1 |
| acidic and propionic | 0.5 |
| butyric | 1.5 |
| valeric | 7.5 |
| caproic | 1.75 |
| hydroxycaproic | 5.25 |
| oxalic | 1.25 |
| succinic | 0.75 |
| glutaric | 1.75 |
| adipic | 4.75 |

In addition, small quantities of other organic materials, particularly resins, are present.

There has been no lack of experiments to do something with these solutions, because considerable costs are necessary for their destruction. Japanese Pat. No. 68 17 163 describes in which these solutions are first acidified with mineral acids to a pH value of 0.7 to 3, after which the two phases that are produced are separated and the organic phase is then extracted with a halogenated hydrocarbon. The extract is stripped of solvent by evaporation and the residue is separated into individual monocarboxylic acids by fractionation. This process cannot operate economically, since out of 3000 kg of waste salt solution, with addition of 400 kg of sulfuric acid only 130 kg of monocarboxylic acids are obtained.

A better proposal is made in Polish Pat. No. 54,750, in which the waste salt solution is at first likewise treated with sulfuric acid, in this case neutralized to a pH value of 5, and then cooled to 18° C. Two phases form, of which the upper organic phase is separated and distilled with steam. This distillate also divides itself into two phases, of which the upper organic phase is then fractionated. Valeric and caproic acids are obtained as products. Here also there is the disadvantage, however, that with a relatively high expense only two substances can be obtained as products and the other materials in the waste salt solution not merely go to waste, but give rise to high additional expenses for their disposition by destruction.

A substantial step forward is represented by the treatment process described in Austrian Pat. No. 313,249. Here the waste salt solution is first acidified with a strong acid and the carboxylic acids are thereby set free. Two phases are formed, a concentrated sodium sulfate solution and a water-containing carboxylic acid mixture, both of which are subjected to further treatment. The carboxylic acids still dissolved in the sodium sulfate solution are removed by an extraction and thereby reclaimed, while the carboxylic acid mixture of the other phase is distilled, producing a distillate containing the water and the volatile monocarboxylic acids and a residue remaining in the pool consisting of dicarboxylic and hydroxycarboxylic acids. The monocarboxylic acids are esterified with isobutanol, wheras the discarboxylic and hydroxycarboxylic acids are esterified with methanol. The esters of the monocarboxylic acids, of the discarboxylic acids and of the hydroxycarboxylic acids can all be used as solvents.

This last-mentioned process provides a genuine advance because in the manner described it is possible to convert the waste salt solution practically entirely into saleable products. On account of the larger quantity of saleable products, it is possible to gain not only more gross income from the operation, but also to save the costs of an otherwise necessary destruction operation and its apparatus for the unsaleable products.

Surprisingly it has now been found that the substantial simplification of the mode of operation of the process of Austrian Pat. No. 313,249 can be accomplished, this simplification having been made possible by the present invention.

SUMMARY OF THE INVENTION

Briefly, the mixture obtained by acidifying the waste salt solution followed by separation of the sodium sulfate solution is first freed of the water still contained therein by distillation in vacuum, in the course of which a certain quantity of the lower boiling monocarboxylic acids are distilled off with the water. The residue is then cooled down to a temperature between $-10°$ C and $+5°$ C, thereby causing a rather large quantity of crystals to be precipitated, which are then separated by filtration or centrifuging. These crystals consist of the dicarboxylic acids that were contained in the raw acid mixture, therefore principally adipic, succinic and glutaric acids. The mother liquor from which these crystals are precipitated then still contains the higher monocarboxylic acids, including 6-hydroxycaproic acid. The further division of this mixture can be carried out by esterification and distillation or fractional distillation.

If the water is not separated before crystallization, no crystals are obtained upon cooling. Even in the water-free solution crystallization begins only at about $+8°$ C and the larger quantities of crystals are obtained only at temperatures below $+5°$ C. Cooling below $-10°$ C is inappropriate, since at lower temperatures the quantity of the crystals does not increase while at the same time, on account of the increasing viscosity of the remaining mother liquor the subsequent separation of the crystals by filtration or centrifuging becomes more difficult.

The crystals obtained can be either esterified directly, followed by separation by a fractional distillation, or they can be treated by known purification processes, as for example recrystallization, to produce pure products.

The advantage of the process of the present invention lies in the fact that in this manner the difficult subsequent separation of the ester of dicarboxylic acids from the ester of 6-hydroxycaproic acid is substantially facilitated, because, although the dicarboxylic acids are not fully separated by the crystallization, they are removed in large part beforehand.

EXAMPLE I

A waste salt solution of cyclohexanone manufacture had the following analysis:

| Material | Percent by Weight |
| --- | --- |
| Water | 62 |
| dry material | 38 |
| organic material | 26.6 |
| sodium, calculated as NaOH | 15.6 |

The organic material consisted of the following components:

| | |
| --- | --- |
| Formic acid | 6.0 % by weight |
| acetic acid | 2.0 |
| propionic acid | 1.2 |
| butyric acid | 4.0 |
| valeric acid | 19.0 |
| caproic acid | 5.0 |
| 6-hydroxycaproic acid | 17.0 |
| succinic acid | 2.0 |
| glutaric acid | 2.8 |
| adipic acid | 19.0 |
| unidentified materials, resins | 22.0 |

20 kg of this solution were mixed with 3.82 kg of sulfuric acid (98%) and the reaction mixture separated into an upper organic phase and a lower aqueous phase. The organic phase weighed 5.6 kg.

This organic phase was fractionated in a thin-layer evaporator at a pressure of 150 Torr until a pool temperature of 67° C was reached, producing 1.0 kg of distillate consisting chiefly of water.

The residue after this distillation was cooled with stirring to +5° C at which time crystallization set in. After 4 hours the material was filtered with a cooled suction filter, after which 0.9 kg of moist crystals remained, consisting primarily of adipic acid. After recrystallization out of hot water 0.75 kg of pure adipic acid was obtained.

The mother liquid from the crystallization, amounting to 3.7 kg, was esterified with methanol in the usual way.

The resulting mixture of esters was then subjected to fractional distillation, by which it was possible to obtain the methyl ester of 6-hydroxycaproic acid substantially free of the more volatile esters of monocarboxyl acids and likewise free of the dicarboxy acids and their esters which remained in the mother liquor. This distillation was carried out at a temperature of 85° C and a pressure of 1.5 Torr.

EXAMPLE II

The procedure of Example I was carried out and thereafter the residue of the second fractional distillation was subjected to esterification with methanol in the usual way, to esterify any free acid liberated in the pool during the second distillation step.

EXAMPLE III

The starting material of Example I was treated as in Example I up to but not including the esterification step. Then the mother liquor from the crystallization (3.7 kg) was subjected to fractional distillation in two stages, a first state at 100° C and 0.007 atm. and a second, with steam from recycled water, at 100° C and 0.2 atm. to recover the 6-hydroxycaproic acid and the other monocarboxy acids as distillates and thereby separate them from the impure residual dicarboxy acids of the residue.

If it is desired to obtain the ester of the monocarboxy and hydroxy acids rather than the free acids, it is preferred to perform the esterification, as in Example I, before the second distillation step. It is also preferred to esterify the residue of the second distillation step, since that facilitates obtaining the dicarboxy acid components sufficiently free of the resins and other miscellaneous residues to constitute saleable products.

The second distillation in the process of the present invention, that is, the distillation that follows the cooling and the separation of the precipitated crystals, is preferably carried out in accordance with the principles of the process disclosed in my copending patent application Ser. No. 516,658, filed Oct. 21, 1974. That process involves three different pressure stages, the first under moderate vacuum, the second under relatively high vacuum and the third again at moderate vacuum. Since in the process of the present invention, however, the water will have been removed by the first distillation preceding the cooling step, the utilization of the invention of my aforesaid co-pending application in connection with the practice of the present invention includes the possibility of proceeding at once, as in Example III, to the high vacuum distillation (at a pressure of 0.002 to 0.02 atm.) at a temperature of under 120° C, followed by distillation at a temperature between 80° C and 120° C at a pressure of 0.1 to 0.3 atm., with recycling of water from the aqueous phase of a previous distillate back into the vaporizer of the distilling apparatus in order to provide steam for this final stage of the distillation, as set forth in my aforesaid copending patent application. This performance of the final distillation of the present invention in distinct pressure stages in accordance with the invention of my aforesaid co-pending application applies particularly to the case where the organic acids are distilled without previous esterification and in which a high degree of separation of the monocarboxylic acids from the dicarboxylic acids is desired. In other cases it is quite practical to carry out the entire distillation at a pressure between 0.0013 atm. and 0.07 atm. and at a temperature between 80° C and 120° C. Above 120° C there is a risk of polymerization of the hydroxy acid. Of course, even in these other cases the technique of a high vacuum distillation followed by a moderate vacuum distillation aided by the steam formed by recycled water from the aqueous phase of an earlier distillate, could also be used to good effect.

The first distillation, preceding the cooling step, must of course be carried out at a temperature below 120° C and it may be carried out at much lower temperatures, preferably in the range of 50° C to 80° C, at a pressure of 0.13 atm. to 0.52 atm.

I claim:

1. In a process for producing esters of monocarboxylic acids and also dicarboxylic acids or their esters from the waste aqueous solution of cyclohexanone manufacture which consists essentially of salts of monocarboxy and dicarboxy straight chain aliphatic acids and of hydroxycaproic acid, comprising the steps of acidifying such a waste salt solution with a strong acid to produce an aqueous phase and an organic phase and then separating a water-containing fraction from the resulting organic phase by distillation at temperatures up to 120° C, followed by esterification of said water-containing fraction with a lower alcohol, the improvement whereby said distillation is accomplished in two distillation steps in a sequence of steps comprising the following:

a first distillation step in which mainly water is distilled off;

cooling the residue of said first distillation step to a temperature between +5° C and −10° C;

separating crystals of solid dicarboxylic acids precipitated in the cooling step, and a second distillation step performed with fractionation at temperatures up to 120° C using the liquid remaining after removal of the crystals, for separation of the more volatile components both from a hydroxyacid fraction recoverable as a separate fraction and from the dicarboxylic acids that remain in the liquid residue.

2. Improvement in a process as defined in claim 1 in which after the precipitated crystals of dicarboxylic acids are separated, the acids remaining in the liquid are esterified with a lower aliphatic alcohol and the second distillation step is carried out with the product of the aforesaid esterification to separate the more volatile esters both from a hydroxyacid ester fraction and from a residue containing dicarboxy acid esters.

3. Improvement in a process as defined in claim 1 in which the residue of the second distillation step is then esterified with a lower aliphatic alcohol.

4. Improvement in a process as defined in claim 2 in which the residue of the second distillation step is likewise esterified with a lower aliphatic alcohol.

5. Improvement in a process as defined in claim 1, in which the second distillation step is carried out at a temperature in the range between 80° C and 120° C and at a pressure between 0.0013 atm. and 0.01 atm.

6. Improvement in a process as defined in claim 1, in which the second distillation step is carried out in two pressure stages, both at a temperature between 80° C and 120° C, the first stage at a pressure in the range between 0.002 and 0.02 atm. and the second at a pressure of between 0.1 and 0.3 atm., said second stage being carried out in the presence of steam provided by recycling of water that was distilled off in an earlier step of the process.

7. Improvement in a process as defined in claim 1, in which the second distillation step is carried out at a temperature between 80° and 120° C in three different pressure stages, the first under moderate vacuum, the second at a pressure in the range between 0.002 and 0.02 atm. and the third at a pressure between 0.1 and 0.3 atm., the third pressure stage of the distillation being performed in the presence of steam provided by recycling water distilled off in a previous step of the process.

8. Improvement in a process as defined in claim 1, in which said first distillation immediately preceding the cooling step is carried out at a temperature in the range from 50° C to 80° C at a pressure in the range from 0.13 atm. to 0.52 atm.

* * * * *